United States Patent
Mayoue

(10) Patent No.: US 10,467,462 B2
(45) Date of Patent: Nov. 5, 2019

(54) SYSTEM AND METHOD FOR DETECTING AT LEAST ONE TRANSIENT PHASE IN A STEADY ACTIVITY OF AN ANIMATED BEING

(71) Applicants: MOVEA, Grenoble (FR); Commissariat à l'energie Atomique et aux Energies Alternatives, Paris (FR)

(72) Inventor: Aurlién Mayoue, Soy sur Seine (FR)

(73) Assignees: Commissariat à l'énergie atomique et aux énergies alternatives, Paris (FR); Movea, Grenoble (FR)

( * ) Notice: Subject to any disclaimer, the term of this patent is extended or adjusted under 35 U.S.C. 154(b) by 793 days.

(21) Appl. No.: 14/365,209

(22) PCT Filed: Dec. 14, 2012

(86) PCT No.: PCT/EP2012/075503
§ 371 (c)(1),
(2) Date: Jun. 13, 2014

(87) PCT Pub. No.: WO2013/092405
PCT Pub. Date: Jun. 27, 2013

(65) Prior Publication Data
US 2014/0343894 A1 Nov. 20, 2014

(30) Foreign Application Priority Data
Dec. 19, 2011 (FR) ...................... 11 61864

(51) Int. Cl.
*G06K 9/00* (2006.01)
*A61B 5/11* (2006.01)
*G06K 9/62* (2006.01)

(52) U.S. Cl.
CPC .......... *G06K 9/00342* (2013.01); *A61B 5/112* (2013.01); *A61B 5/1122* (2013.01);
(Continued)

(58) Field of Classification Search
CPC . A61B 2503/09; A61B 2503/10; A61B 5/112; A61B 5/1122; A61B 5/1123;
(Continued)

(56) References Cited

U.S. PATENT DOCUMENTS 4,932,045 A 6/1990 Kasoff et al.
6,571,193 B1 5/2003 Unuma et al.
(Continued)

FOREIGN PATENT DOCUMENTS

EP 1870139 12/2007
EP 2236987 10/2010
(Continued)

OTHER PUBLICATIONS

Koskimaki, Activity Recognition Using a Wrist-worn Inertial Measurement Unit: a case study for industrial assembly lines, Jun. 2009.*
(Continued)

*Primary Examiner* — Michael P Nghiem
*Assistant Examiner* — Dacthang P Ngo
(74) *Attorney, Agent, or Firm* — BakerHostetler

(57) ABSTRACT

A system for detecting at least one transient phase in a steady activity of an animated being includes processing circuitry for determining signals representative of the motion of the animated being along at least one axis, for calculating a resultant signal representative of a statistical link between samples of signals representative of the motion belonging respectively to at least two temporally offset sliding windows over the samples, and for detecting a transient phase on the basis of the resultant signal.

17 Claims, 8 Drawing Sheets

(52) U.S. Cl.
CPC .......... *A61B 5/1123* (2013.01); *G06K 9/0055* (2013.01); *G06K 9/6284* (2013.01); *A61B 2503/10* (2013.01); *A61B 2505/09* (2013.01)

(58) Field of Classification Search
CPC .... G06K 9/0055; G06K 9/6284; B61B 5/112; B61B 5/1122; B61B 5/1123
USPC .......................................................... 702/179
See application file for complete search history.

(56) References Cited

U.S. PATENT DOCUMENTS

| 2007/0293374 | A1  | 12/2007 | Chan   |            |
|--------------|-----|---------|--------|------------|
| 2011/0046498 | A1* | 2/2011  | Klap   | A61B 5/0205 |
|              |     |         |        | 600/534    |
| 2012/0041713 | A1* | 2/2012  | Bonnet | A61B 5/1038 |
|              |     |         |        | 702/160    |
| 2012/0101785 | A1* | 4/2012  | Jallon | A61B 5/1116 |
|              |     |         |        | 703/2      |
| 2012/0191408 | A1* | 7/2012  | Godin  | A61B 5/103 |
|              |     |         |        | 702/150    |

FOREIGN PATENT DOCUMENTS

| WO | WO2010097422   | * | 9/2010  |
|----|----------------|---|---------|
| WO | 2010/122173    |   | 10/2010 |
| WO | WO 2010/122173 | * | 10/2010 |
| WO | 2011/012666    |   | 2/2011  |
| WO | WO 2011/012666 | * | 3/2011  |

OTHER PUBLICATIONS

Vathsangam, An Experimental Study in Determining Energy Expenditure from Treadmill Walking using Hip-worn Sensors, Jun. 2011.*
Kinnunen, Efficient Accelerometer-Based Swimming Exercise Tracking, Apr. 2011 (Year: 2011).*
International Search Report and Written Opinion from PCT/EP2012/075503, dated Mar. 22, 2013.

* cited by examiner

SYSTEM AND METHOD FOR DETECTING AT LEAST ONE TRANSIENT PHASE IN A STEADY ACTIVITY OF AN ANIMATED BEING

Embodiments of the invention relate to a system and a method for detecting at least one transient phase in a steady activity of an animated being, based on signals representative of the motion of the animated being, such as a human or a mobile robot.

BACKGROUND

Field of Invention

A steady activity is defined by statistical characteristics of the activity that do not vary translationally in time, such as the moments of order k, and more particularly the moments of order 1 (for example an average) and the moments of order 2 (for example a correlation).

Examples of steady activities that can be cited include, without being exhaustive, the following activities: racing, swimming, horse riding, body building, etc. These activities in fact exhibit steady phases during which the statistical characteristics remain unchanging in time. They can, however, be interspersed with so-called transient phases during which the animated being changes its activity.

The transient phase corresponds to a state during which the steady activity of the animated being is disrupted, and during which there is a change of the statistical properties. A transient phase can occur in different forms, for example in the form of an obstacle to be overcome (hurdles to be jumped in a sprint or obstacles to be jumped in a horse riding session), a change of direction or of heading of the animated being (change of direction in a series of lengths executed by a swimmer or a racer), or a brief change of activity envisaged by the animated being to interrupt its steady activity (series of bends/extensions when jogging). It is thus possible to find different transient phases in one and the same steady activity. Take, for example, a jogging session in straight lines interrupted by bends/extensions and marked by changes of direction at the end of each straight line. There is an interest in being able to provide the player of the activity with information on this activity, automatically and objectively, by detecting and by counting the number of occurrences of events in the activity. Thus, the detection and counting of the transient phases in an activity may constitute relevant information for the player of the activity.

Description of Related Art

The American patent application U.S. Pat. No. 4,932,045 relates to a system which counts lengths, but with manual intervention on the part of the swimmer. The counter, fixed to the hand or the foot of the swimmer, has to be pressed against the wall of the swimming pool on each turn of the swimmer in order to be incremented by one unit. This device can disrupt the swimming of the athlete.

The American patent application US 2007/0293374 A1 discloses a system that makes it possible to automatically count the lengths of a swimmer without the manual intervention thereof. The go/return counter comprises a box, means for fixing the box to the swimmer, a compass sensor internal to the box to provide an output signal which changes at the time of the turn of the swimmer (i.e. as a function of the go or return direction of the swimmer in the swimming pool) and a processor programmed to detect, in the output signal from the sensor, the change of direction of the swimmer and count the number of go and return lengths of the swimmer.

Such a system includes a certain number of turn detection errors.

SUMMARY

One aim of embodiments of the invention is to propose a system and a method for detecting at least one transient phase in a steady activity of an animated being, it notably makes it possible to improve the detection efficiency of the system by reducing the number of false detections and non-detections, without increasing its computation cost.

Thus, there is proposed, according to one aspect of the invention, a system for detecting at least one transient phase in a steady activity of an animated being, comprising means for determining signals representative of the motion of said animated being along at least one pathway, means for calculating a resultant signal representative of a statistical link between samples of said signals representative of said motion belonging respectively to at least two temporally offset sliding windows over said samples, and means for detecting a transient phase on the basis of said resultant signal.

The means for determining signals representative of the motion may include motion sensors borne by the animated being, for example sensors of accelerometer, magnetometer or gyrometer type. It is also possible to use means installed in the environment in which the motions are performed. For example optical, electromagnetic motion capture means.

Such a system makes it possible, at low cost, to detect at least one transient phase in a steady activity of an animated being.

According to one embodiment, the system comprises means for filtering said signals representative of said motion upstream of said calculation means.

The filtering means make it possible to select, within said signals representative of said motion, the spectral components of interest and to focus the ensuing processing on the spectral components that are mostly representative of the interruption of the steady activity.

For example, said sliding windows partially overlap.

Thus, the time trend of the statistical link between the samples obtained from said sliding windows will be able to be calculated more accurately than when there is no overlap. This will ultimately allow for a more accurate detection of the transient phases.

Furthermore, said sliding windows can be of the same size.

Thus, the calculation of the statistical link is simplified because it is performed without the addition or subtraction of samples in said sliding windows.

In one embodiment, the temporally ordered sliding windows respectively indexed from 1 to F are temporally spaced apart so as to observe the following relationship:

$$T_1 + D_F \leq S$$

in which:
  $T_1$ represents the duration of the first window indexed 1,
  $D_F$ represents the offset between the first window indexed 1 and the last window indexed F, and
  S corresponds to a minimum duration of the steady activity between two successive transient phases.

Thus, there is at least one instant between two successive transient phases for which the statistical link is calculated on the basis of samples that all originate from the same steady phase. At these instants, the amplitude of the resultant signal, representative of the statistical link, will be minimal and will be able to be used to identify and separate the different types of phases.

According to one embodiment, when said signals representative of the motion are determined along at least two measurement pathways, the system comprises means for merging the components on each pathway of said resultant signal.

Thus, it is possible to increase the transient phase detection efficiency, by multiplying the measurements of the motion and thus by increasing the probability that they relate to the statistical break due to the transient phase of the motion. The merging means then make it possible to reduce the situation to the case with one component by merging the useful information obtained from all the measurement pathways.

For example, said merging means can be adapted to calculate the sum of the components along each pathway of said resultant signal.

It is thus possible to condense the information less expensively.

In one embodiment, said detection means are adapted to:
  detect a first transient phase in the steady activity when the resultant signal along a single pathway or the merged signal output from the merging means becomes greater than a first threshold; and
  detect another transient phase in the steady activity when the resultant signal along a single pathway or the merged signal output from the merging means, since the last detection of a transient phase, has been lower than a second threshold and then is higher than said first threshold;
said second threshold being lower than said first threshold.

It is thus possible to detect a series of transient phases in the steady activity.

According to one embodiment, the system comprises differentiation means adapted to establish a difference between two instants of said signals representative of the motion, and means for determining the maximum energy component of the differentiated signals, said detection means being adapted to detect another transient phase in the steady activity when, in addition, the sign of said maximum component, when the merged signal is above said first threshold, is opposite to the sign of said maximum component upon the preceding detection.

The detection accuracy is thus enhanced.

Furthermore, the system can comprise means for counting the number of transient phases.

Thus, in addition to detecting the transient phases, the system can count them and also provide the instant of occurrence of the transient phase in time.

Furthermore, the system can comprise means for timing the transient and/or steady phases.

Many racers want to know the number of sprints performed in a split session (series of sprints performed over a fixed distance or time and interspersed with brief rest periods in jog-trotting form). Generally, the runner is set a number of sprints to be completed in advance in order to validate the training session. Now, it is not always easy to perform this physical exercise while mentally counting the number of sprints performed. The fact of having a system which automatically detects and counts the transient phases (corresponding in this case to the jog-trotting phases) which intersect the sprints enables the runner to improve the conditions in which the training takes place.

In one embodiment, said detection means are adapted to detect half-turns of a person, between two courses of a straight line in opposite directions, or to detect changes of direction of a person on a course comprising a series of straight lines.

According to one embodiment, provided with a sealed box comprising said means for determining signals representative of the motion of a swimmer and fixing means for securely linking said box to a part of the body of said swimmer, said steady activity being the swimming of a swimming pool length and the transient phase being a half-turn.

For example, said counting means are adapted to count the go and return lengths of a swimmer in a swimming pool.

In practice, many swimmers want to be able to accurately assess the distance that they have travelled in a swimming session. Generally, the length completed is known to the practicing party and corresponds, for him or her, to an informed distance. However, the fact of having to count the number of lengths or go and return lengths is tedious, includes a not-inconsiderable risk of error and, for a good swimmer, may disrupt him or her and limit his or her performance. A method of counting the transient phases (here, the turns of the swimmer) which intervene between each length makes it possible to solve these problems. Furthermore, in addition to automatically counting the number of lengths completed, the invention makes it possible to provide the instant of each turn and thus makes it possible to add to the counting information supplied to the swimmer.

For example, said calculation of the statistical link comprises a covariance function.

According to another aspect of the invention, there is also proposed a method for detecting at least one transient phase in a steady activity of an animated being, in which signals representative of the motion of said animated being are determined along at least one axis, and a resulting signal representative of a statistical link between samples of signals representative of said motion belonging respectively to at least two temporally offset sliding windows over said samples is calculated.

BRIEF DESCRIPTION OF THE DRAWINGS

The invention will be better understood on studying a few embodiments described as non-limiting examples and illustrated by the attached drawings in which.

DETAILED DESCRIPTION OF THE INVENTION

Figure 1:
FIGS. 1 to 5 schematically illustrate embodiments of a system, according to one aspect of the invention.

In FIG. 1, the system for detecting at least one transient phase in a steady activity of an animated being, according to one embodiment of the invention, comprises a module DETER for determining signals representative of the motion of said animated being along at least one axis, a module CALC for calculating a resultant signal representative of a statistical link between samples of said signals representative of said motion belonging respectively to at least two temporally offset sliding windows, and a module DETEC for detecting a transient phase on the basis of said resultant signal.

Figure 2:
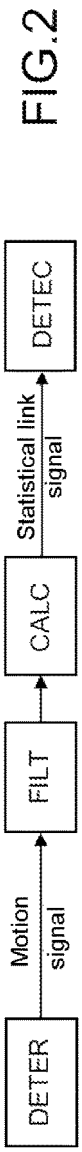

An optional module FILT for filtering said signals representative of said motion upstream of said calculation means, as represented in FIG. 2.

For example, the sliding windows can partially overlap, and/or be of the same size.

Furthermore, the temporally ordered sliding windows respectively indexed from 1 to F are temporally spaced apart so as to observe the following relationship:

$$T_1 + D_F \leq S$$

in which:
T$_1$ represents the duration of the first window indexed 1,
D$_F$ represents the offset between the first window indexed 1 and the last window indexed F, and
S corresponds to a minimum duration of the steady activity between two successive transient phases.

Figure 3:

Furthermore, as illustrated in FIG. 3, the system can comprise a module FUS for merging the components on each pathway of said resultant signal, for example adapted to calculate the sum of the components along each pathway of said resultant signal.

Furthermore, the detection module DETEC can be adapted to:
detect a first transient phase in the steady activity when the resultant signal along a single pathway or the merged signal output from the merging means FUS becomes greater than a first threshold Seuil_1; and
detect another transient phase in the steady activity when the resultant signal along a single pathway or the merged signal output from the merging means FUS, since the last detection of a transient phase, has been lower than a second threshold Seuil_2 than is higher than said first threshold Seuil_1;
said second threshold Seuil_2 being lower than said first threshold Seuil_1.

Said thresholds Seuil_1 and Seuil_2 can depend on the measurement range of the sensor or sensors used to acquire said signals representative of the motion, and/or are set by learning from a base of motion signals recorded by the sensor or sensors.

Figure 4:
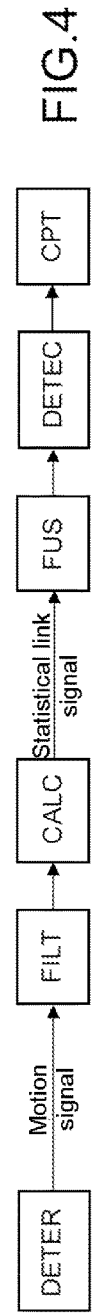

Furthermore, the system can comprise a module CPT for counting the number of transient phases, as illustrated in FIG. 4.

The detection module DETEC can be adapted to detect half-turns of a person, between two crossings of a straight line in opposite directions.

For example, the system can comprise a sealed box comprising the means DETER for determining signals representative of the motion of a swimmer and fixing means for securely linking the box to a part of the body of the swimmer, said steady activity being the swimming of a swimming pool length and the transient phase being a half-turn. The counting module CPT can be adapted to count the go and return lengths of a swimmer in a swimming pool. Also, the counting module can deduce therefrom the number of lengths travelled, therefore the distance that has been swum. It can also provide the instants corresponding to the half-turns detected. It will be possible to deduce therefrom an average swimming speed, for example, over one or more lengths.

The calculation of the statistical link can, for example, comprise a covariance function.

Figure 5:
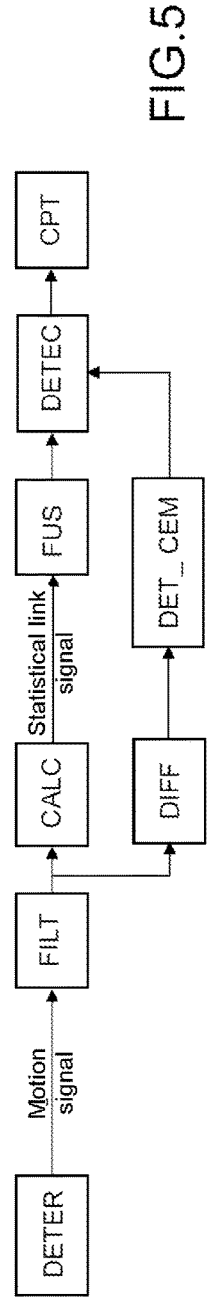

Furthermore, as illustrated in FIG. 5, the system can comprise a differentiation module DIFF adapted to establish a difference between two instants t and t+Δt (with Δt<S) of the signals representative of the motion, and a module DET_CEM for determining the maximum energy component of the differentiated signals. The detection module DETEC is then adapted to detect another transient phase in the steady activity when, in addition, the sign of said maximum component, when the merged signal is above the first threshold Seuil_1, is the opposite of the sign of the maximum component upon the preceding detection. The energy of a signal corresponds to the sum of its samples squared. The number of false detections is thus limited.

The following example is described in a non-limiting manner.

The embodiment calculation module CALC is adapted to supply a signal resulting from a function which captures the statistical relationship between the parts of the signals obtained from at least two temporally offset sliding windows, from at least one signal representative of the motion covered by the sliding windows. The resultant signal is characterized by peaks at the time of the transient phases and transitions through values close to zero during the steady phases. It is then possible, by setting decision thresholds, to detect and count the transient phases automatically.

For example, it is possible to detect the half-turns in a series of lengths executed by a swimmer or a sprinter. For example, the signals representative of the motion are obtained from a triaxial magnetometer worn by the sports person. Also, the determination module DETER comprises the triaxial magnetometer.

Figure 6:
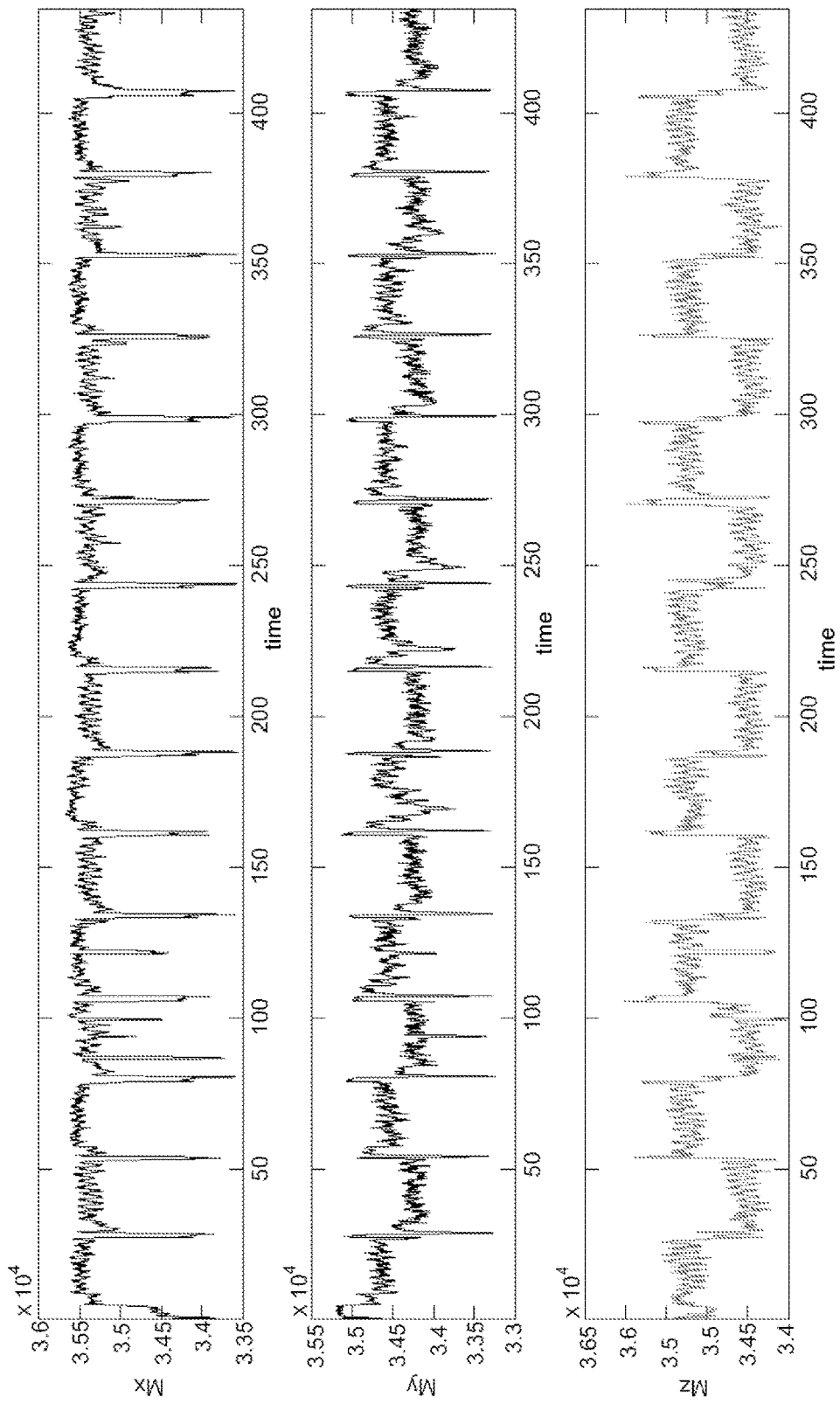
FIGS. 6 to 13 illustrate signals corresponding to the processing operations implemented by the system of FIG. 4, according to one embodiment of the invention.

The triaxial magnetometer of the determination module DETER fixed to the body of the swimmer or of the sprinter (head, back, ankle or wrist) supplies a sample signal M$_i$(t), i∈{x, y, z}, t∈ℕ which changes as a function of the go or return direction of the sports person. The signal Mx, My, Mz on the three axes x, y and z of the magnetometer is represented in FIG. 6, corresponds to the measurement of sixteen steady phases intercepted by fifteen transient phases.

Figure 7:
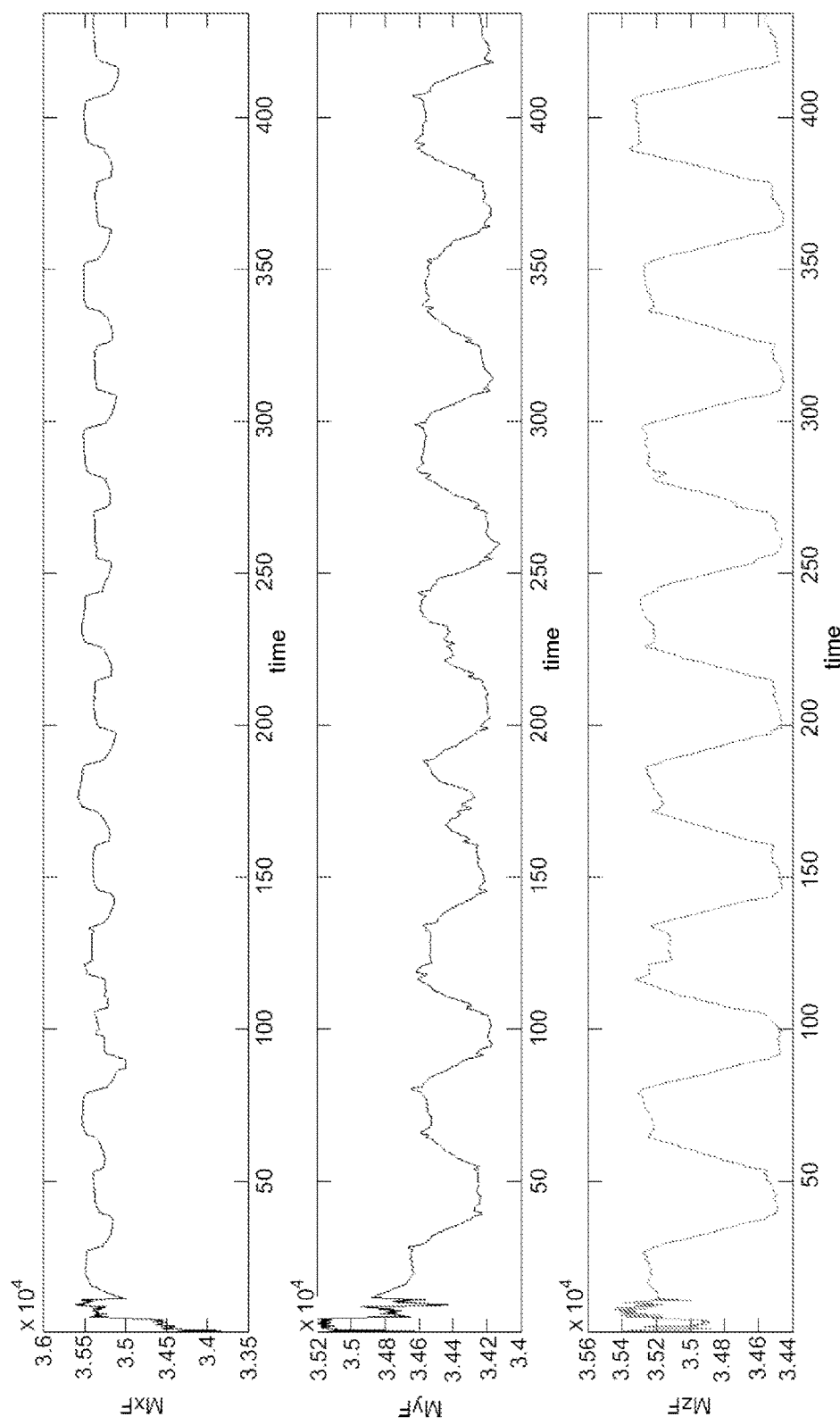

The filtering module FILT makes it possible to attenuate the spurious motions that are not characteristic of the transient phases and which can disturb their detection. These motions appear during the steady activity and are due, in the present example, to the strokes of the swimmer or to the strides of the sprinter. In this case, the filtering can be of bypass type (average filter) in order to eliminate the spurious motions (high frequencies) without affecting the useful low-frequency information linked to the half-turns as illustrated in FIG. 7 for each axis x, y, z:

$$MF_i(t) = \frac{1}{L} \sum_{n=t-L+1}^{t} M_i(n), \, i \in \{x, y, z\}, L \in \mathbb{N}$$

The size L of the sliding window which is for calculating the average is preferably configured such that E<L<S, in which S is the minimum duration of the steady activity between two transient phases and E represents the maximum deviation between two spurious motions.

The filtering step is optional in the processing chain, but its application can make it possible to improve the detection of the transient phases. It is possible to replace the average with other types of filter that make it possible to attenuate or eliminate the components of the signal that correspond to the motions which do not convey information on the transient phase.

Figure 8:
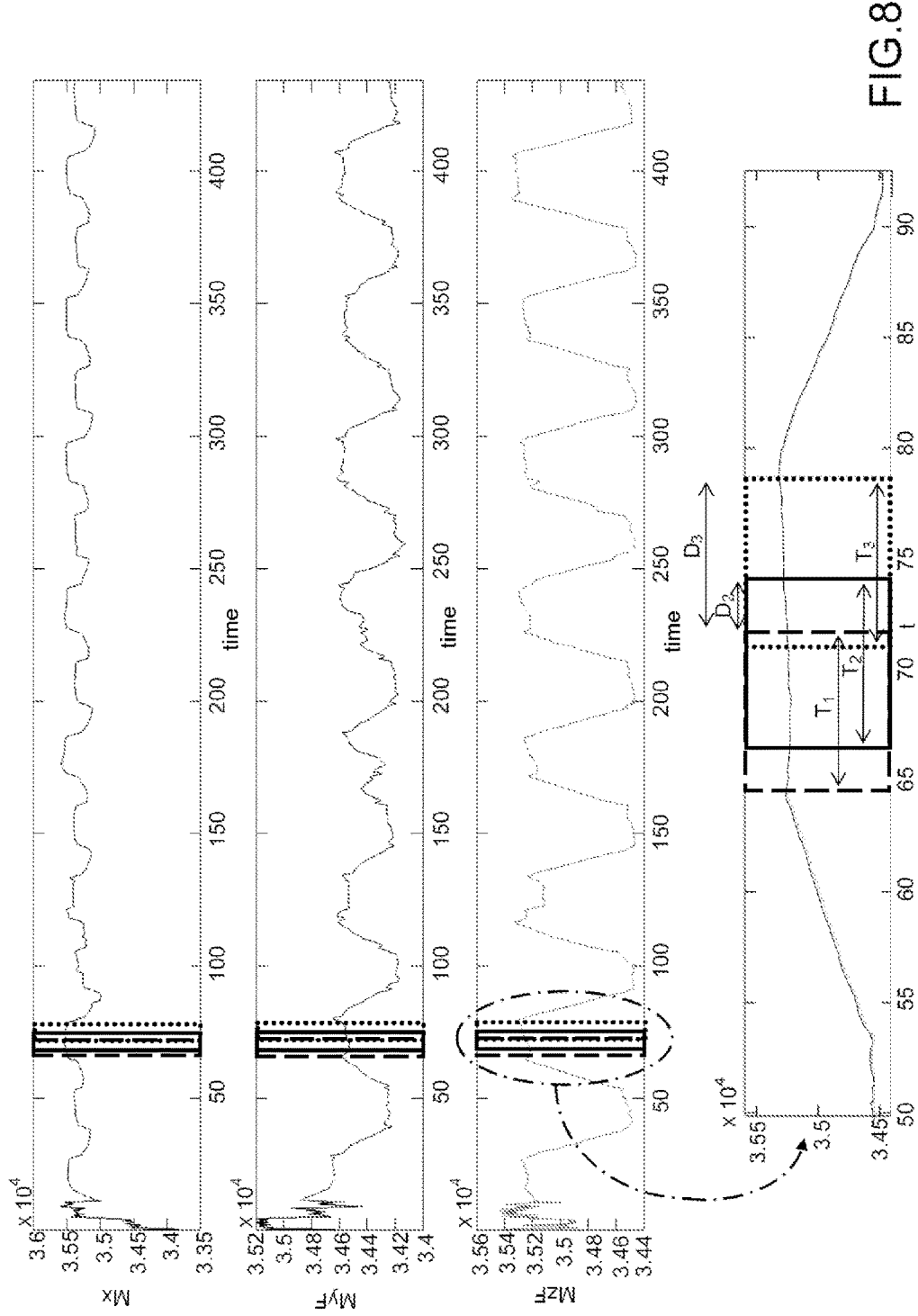

The calculation module CALC performs a windowing, as illustrated in FIG. 8, which includes defining F sliding windows (F∈ℕ*\{1}) which cover the components of the motion signal to be analyzed. The F temporally ordered windows can be positioned in such a way as to observe the following relationship:

$$T_1 + D_F \leq S$$

in which:
T₁ represents the duration of the first window indexed 1,
$D_F$ represents the offset between the last sample of the first window indexed 1 and the first sample of the last window indexed F, and
S still represents the minimum duration of the steady activity between two transient phases.

If the first sliding window indexed 1, of size $T_1$ considered at the instant t, picks up the filtered signal MF as follows:

$$MF1_i^{(t)}(k) = MF_i(k+t-T_1), k \in [1;T_1], i \in \{x,y,z\}$$

Then the F−1 other sliding windows indexed j of size $T_j$ pick up the filtered signal MF at the instants $t+D_j$ by observing the following relationship:

$$MFj^{(t+D_j)}(k) = MF_i(k+t+D_j-T_j), k \in [1;T_j], i \in \{x,y,z\}$$

in which $D_j$ represents the offset between the last sample of the first window of index 1 and the window of index j.

By positing $D_1=0$, it is possible to define, generically, the signals picked up by the F sliding windows at a given instant t $$MFj_i^{(t+D_j)}(k) = MF_i(k+t+D_j-T_j), k \in [1;T_j],$$
$$i \in \{x,y,z\}, \forall j \in [1;F]$$

Before estimating the relationship or the statistical link between the signals obtained from the F sliding windows, the situation is reduced to the case in which the signals are all of the same size.

To reduce the situation to the case of signals comprising N samples, it is possible to remove (respectively add), by decimation (respectively by interpolation) $T_j-N$ (respectively $N-T_j$) samples evenly spaced apart (respectively intercalated) within the signal from the window of index j and of initial size $T_j > N$ (respectively $T_j < N$).

The calculation of the statistical link includes calculating a signal MFC resulting from a function f which models, for each measurement axis, the statistical link that exists between the signals of size N from the F sliding windows defined at the instant t as follows:

$$MFC_i(t) = f(MF1_i^{(t)}, \ldots, MFj_i^{(t+D_j)}, \ldots, MFF_i^{(t+D_F)}), i \in \{x,y,z\}$$

Figure 9:
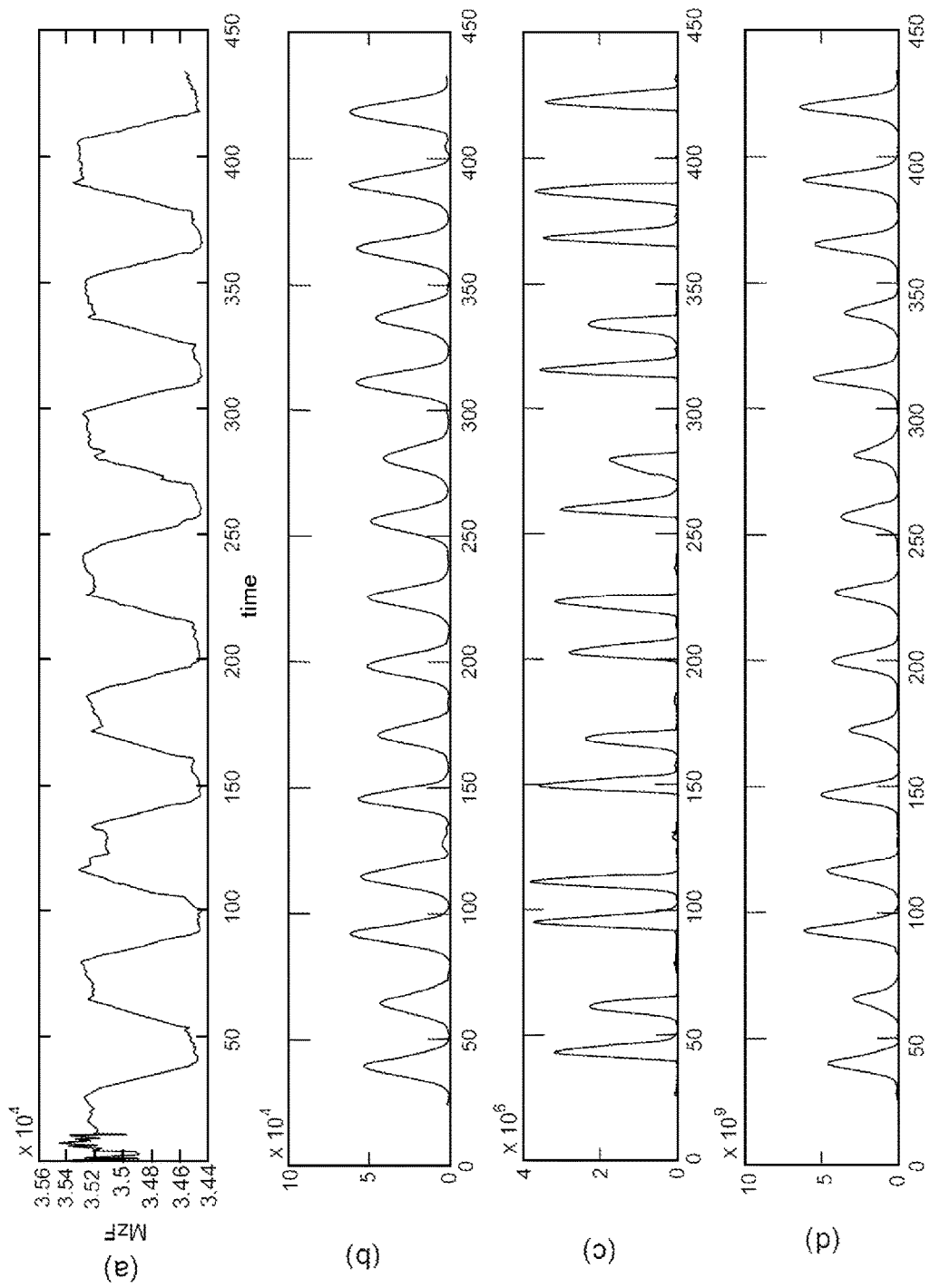

The function f which picks up the statistical link between the signals from the F sliding windows can take the following form:

$$f\left(MF1_i^{(t)}, \ldots, MFj_i^{(t+D_j)}, \ldots, MFF_i^{(t+D_F)}\right) =$$
$$\sum_{n=1}^{N} \prod_{j=1}^{F} \left(MFj_i^{(t+D_j)}(n) - \mu_{j_i}^{(t+D_j)}\right)^{p_j}$$

with $\mu_{j_i}^{(t+D_j)} = \frac{1}{N}\sum_{k=1}^{N} MFj_i^{(t+D_j)}(k)$ and $p_j \in \aleph$ FIG. 9 represents a few examples of signals MFC (with one component) resulting from the function f when the number of sliding windows F is equal to two, for different pairs of values ($p_1$, $p_2$).

The function f picks up the statistical link between the signals from F=2 sliding windows which cover the filtered signal MF with one measurement axis (a). The resulting signal is shown for different values of p1 and p2: p1=p2=1 (b), p1=1 and p2=2 (c), p1=p2=2 (d). In all the cases, the 15 peaks indicate the 15 transient phases.

Figure 10:
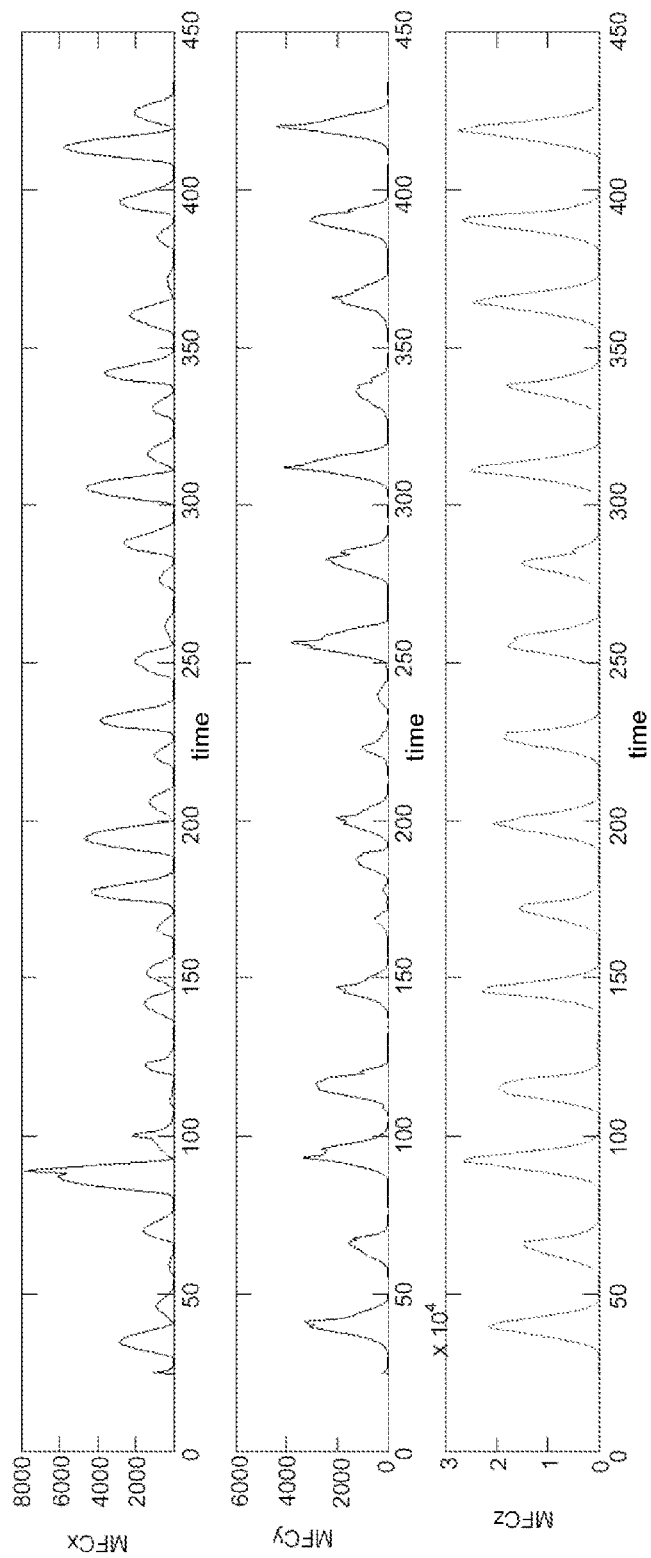

FIG. 10 represents a signal MFC with 3 components obtained in the case where the number of sliding windows F=2 and for which the exponents p1=p2=1. It should be noted that, for which precise case, the function f corresponds to the covariance function.

Figure 11:
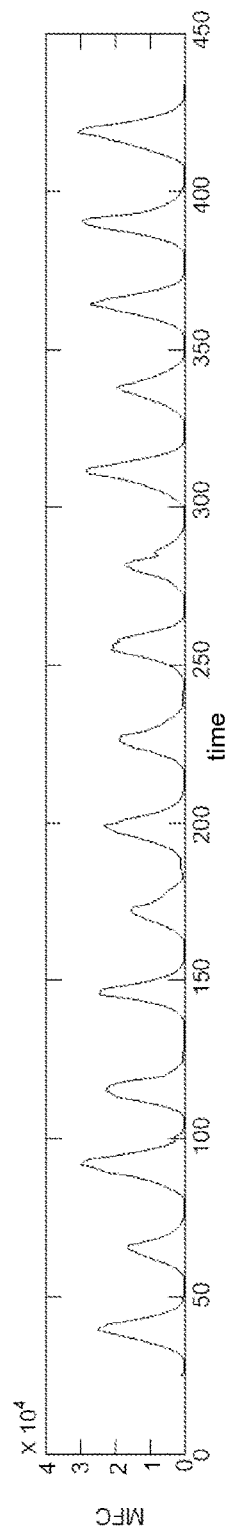

The merging module FUS makes it possible to condense the information by transforming the multi-pathway or multi-component signal, in this case three components, a $MFC_i$, $i \in \{x,y,z\}$ into a signal with a single component MFC with:

$$MFC(t) = \sum_i MFC_i(t)$$

as illustrated in FIG. 11.

Before the detection step, it appears that the merged signal exhibits the characteristics desirable to facilitate the detection of the transient phases, namely: a succession of peaks at the half-turns intercepted by 0 bands during the steady activity (swimming or sprinting phases).

Figure 12:
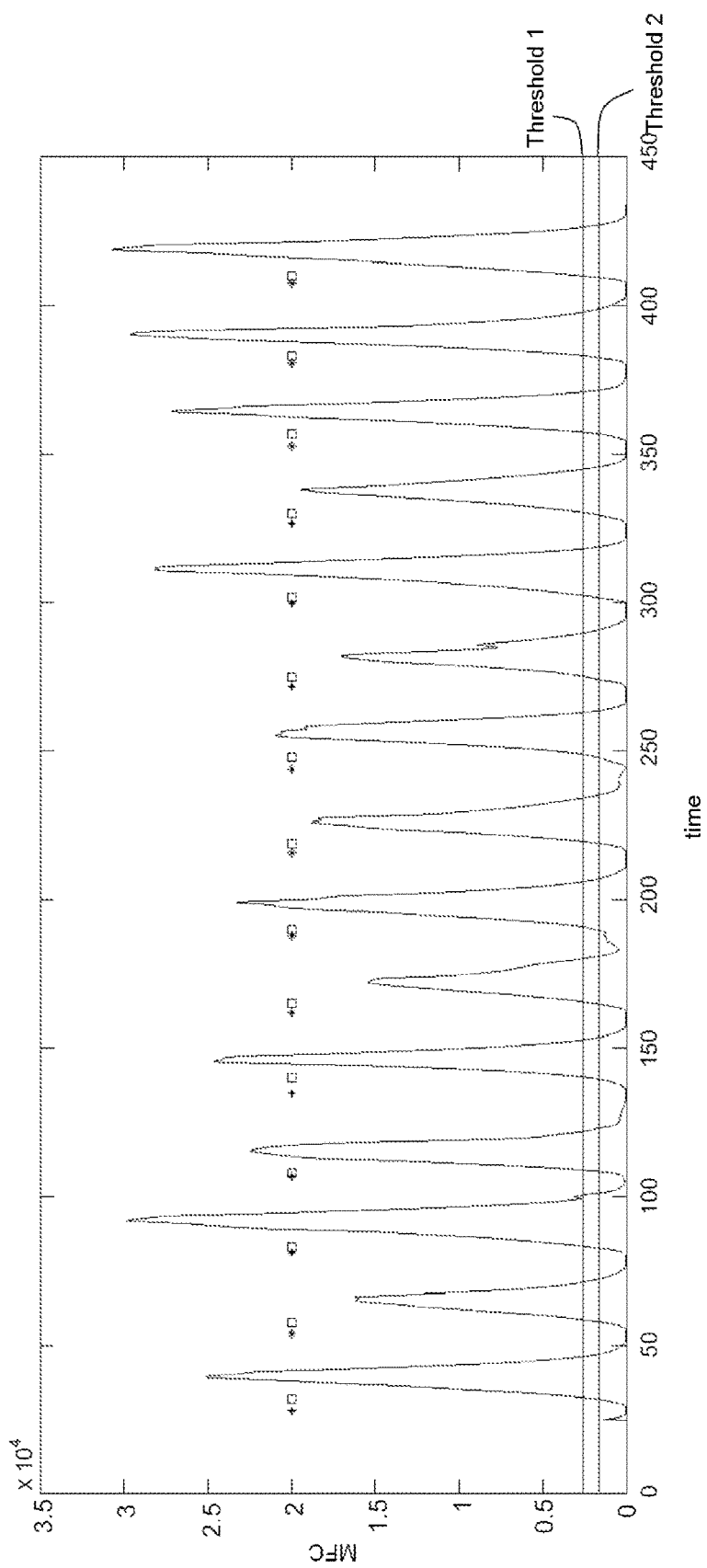

The detection module DETEC detects a first transient phase when the amplitude of the merged signal MFC becomes greater than a first threshold value seuil1. Following a turn numbered j detected at the instant T, a turn numbered j+1 will then be detected at the instant T+1 provided that MFC(T+1)>seuil1 and that the amplitude of the signal has dropped back below a second threshold value seuil2 between the instants T and T+1. In practice seuil1>seuil2 is illustrated in FIG. 12. The threshold values are, for example, defined by learning on an annotated database.

The black stars in FIG. 12 represent the real instants of the half-turns of the sprinter or of the swimmer whereas the squares indicate the instants of the half-turns detected automatically by the system. The horizontal lines respectively symbolize the thresholds seuil1 and seuil2.

Figure 13:
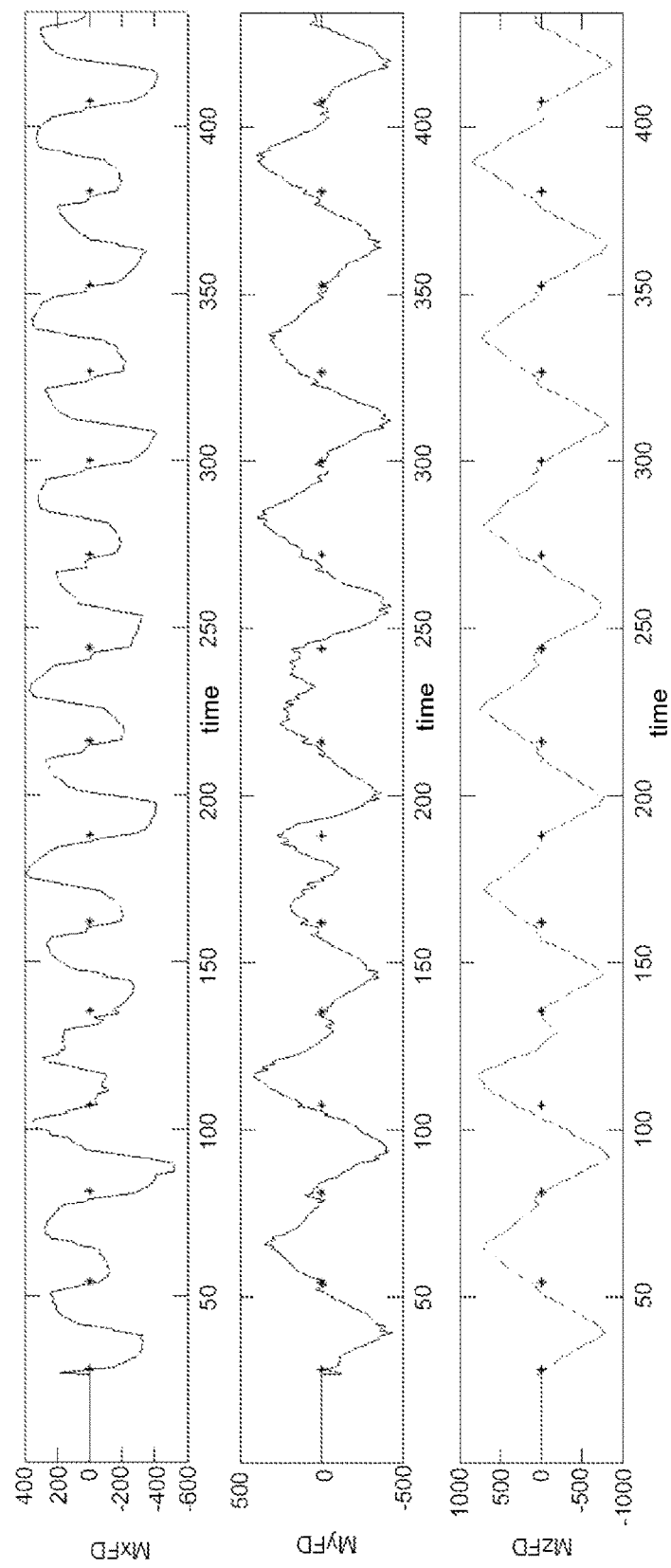

The efficiency with which transient phases are detected by the system can be enhanced by adding an additional constraint at the decision-taking time, for example by involving the sign of the main component (the highest energy component) of the filtered signal, differentiated between the instants t and t−Δt, as illustrated in FIG. 13:

$$MFD_i(t) = MF_i(t) - MF_i(t-\Delta t), \Delta t \in \aleph, i \in \{x,y,z\}$$

Δt being of the same order of magnitude as the size L of the window used for calculating the average.

In the figure, the filtered and differentiated signal with three components has, for the maximum component, the component z, which changes sign on each half-turn.

In addition to the conditions on the amplitude of the signal MFC described previously, a turn can be detected if the sign of the maximum component at the moment when the first threshold seuil1 is exceeded by MFC is different from the sign of this same component during the preceding turn. This additional constraint makes it possible to reduce the number of false detections of transient phases but, on the other hand, does make it necessary to differentiate the signal MF which otherwise is not necessary in the proposed processing chain. It should be noted that the use of this sign, even if it improves the results, is totally optional and does not in any way modify the calculations of the processing chain.

Those skilled in the art will recognize that the present invention has many applications, may be implemented in various manners and, as such is not to be limited by the foregoing embodiments and examples. Any number of the features of the different embodiments described herein may be combined into a single embodiment, the locations of particular elements can be altered and alternate embodiments having fewer than or more than all of the features herein described are possible. Functionality may also be, in whole or in part, distributed among multiple components, in manners now known or to become known.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention. While there has been shown and described fundamental features of the invention as applied to being exemplary embodiments thereof, it will be understood that omissions and substitutions and changes in the form and details of the disclosed invention may be made by those skilled in the art without departing from the spirit of the invention. Moreover, the scope of the present invention covers conventionally known, future developed variations and modifications to the components described herein as would be understood by those skilled in the art.

The invention claimed is:

1. A device, coupled to an animated being, configured for counting transitions along at least one pathway, the device comprising:
   at least one motion sensor;
   processing circuitry configured to receive, from the at least one motion sensor, signals representative of motion of said animated being along the at least one pathway, wherein said signals representative of the motion are determined along at least two pathways, each pathway having at least one component;
   the processing circuitry further configured to determine, based on an electronic assessment of the determined signals, a resultant signal representative of a statistical link between samples of said signals representative of said motion belonging respectively to at least two temporally offset sliding windows over said samples, wherein a steady activity includes an invariance of the statistical link of the samples of said signals representative of said motion, wherein the processing circuitry is further configured to merge the at least one component on each pathway of said resultant signal;
   the processing circuitry further configured to detect at least one transient phase of a plurality of transient phases, based on an electronic assessment of said resultant signal, each transient phase corresponding to a transition from a first pathway to a second pathway during which there is a modification of the statistical link of the samples of said signals representative of said motion, wherein the second pathway is in a different direction than the first pathway;
   the processing circuitry further configured to generate a count of a number of detected at least one transient phases, wherein the generated count indicates a number of pathways; and
   the processing circuitry further configured to cause the generated count to be sent in an output signal.

2. The device as claimed in claim 1, further comprising:
   the processing circuitry further configured to filter said signals representative of said motion prior to the calculating.

3. The device as claimed in claim 1, wherein said sliding windows partially overlap.

4. The device as claimed in claim 1, wherein said sliding windows are of the same size.

5. The device as claimed in claim 1, wherein the sliding windows, temporally ordered and respectively indexed from 1 to F, are temporally spaced apart so as to observe the following relationship:

$$T_1 + D_F \leq S$$

in which:
   $T_1$ represents a duration of a first window indexed 1,
   $D_F$ represents an offset between the first window indexed 1 and a last window indexed F, and
   S corresponds to a minimum duration of steady activity between two successive transient phases.

6. The device as claimed in 1, wherein the processing circuitry is further configured to calculate a sum of components along each pathway of said resultant signal.

7. The device as claimed in claim 6, wherein the processing circuitry is further configured to:
   detect a first transient phase in steady activity when the resultant signal along a single pathway or a merged signal output becomes greater than a first threshold; and
   detect another transient phase in the steady activity when the resultant signal along the single pathway or the merged signal output, since a prior detection of a transient phase, has been lower than a second threshold and then is higher than said first threshold, wherein said second threshold being lower than said first threshold.

8. The device as claimed in claim 7 wherein the processing circuitry is further configured to establish a difference between two instants of said signals representative of the motion, and configured to determine a maximum energy component of differentiated signals, wherein the processing circuitry is further configured to detect another transient phase in the steady activity when a sign of said maximum component, when the merged signal is above said first threshold, is opposite to a sign of said maximum component in a preceding detection.

9. The device as claimed in claim 1, wherein the processing circuitry is further configured to determine timing of the transient or steady phases.

10. The device as claimed in claim 1 wherein the processing circuitry is further configured to detect half-turns of a person, between two crossings of a straight line in opposite directions, or to detect changes of direction of a person on a course comprising a series of straight lines.

11. The device as claimed in claim 10, wherein the number of pathways indicates to and return lengths of a swimmer in a swimming pool.

12. The device as claimed in claim 1, wherein the processing circuitry is disposed within a sealed box coupled to a portion of a body of a swimmer and is further configured for determining signals representative of motion of said swimmer, said steady activity being swimming of a swimming pool length and the transient phase being a half-turn.

13. The device as claimed in claim 1, wherein the statistical link comprises a covariance function.

14. A method for use in a device, coupled to an animated being, for counting transitions along at least one pathway, the method comprising:
   acquiring, from at least one motion sensor, signals representative of motion of said animated being determined along the at least one pathway, wherein said signals representative of the motion are determined along at least two pathways, each pathway having at least one component;
   determining, based on an electronic assessment of the acquired signals, a resulting signal representative of a statistical link between samples of said signals representative of said motion belonging respectively to at least two temporally offset sliding windows over said samples, wherein a steady activity includes an invariance of the statistical link of the samples of said signals representative of said motion, wherein the at least one component is merged on each pathway of said resultant signal;

detecting at least one transient phase of a plurality of transient phases, based on an electronic assessment of said resultant signal, each transient phase corresponding to a transition from a first pathway to a second pathway during which there is a modification of the statistical link of the samples of said signals representative of said motion, wherein the second pathway is in a different direction than the first pathway;

generating a count of a number of detected at least one transient phases, wherein the generated count indicates a number a number of pathways; and causing the generated count to be sent in an output signal.

15. A device, coupled to swimmer, configured for counting swimming pool lengths, the device comprising:

at least one motion sensor;

processing circuitry configured to receive, from the at least one motion sensor, signals representative of motion of said swimmer being along a swimming pool length, wherein said signals representative of the motion are determined along at least two pathways, each pathway having at least one component;

the processing circuitry further configured to determine, based on an electronic assessment of the determined signals, a resultant signal representative of a statistical link between samples of said signals representative of said motion belonging respectively to at least two temporally offset sliding windows over said samples, wherein a steady activity includes an invariance of the statistical link of the samples of said signals representative of said motion, wherein the processing circuitry is further configured to merge the at least one component on each pathway of said resultant signal;

the processing circuitry further configured to detect at least one transient phase of a plurality of transient phases, based on an electronic assessment of said resultant signal, each transient phase corresponding to a transition from a first swimming pool length to a second swimming pool length during which there is a modification of the statistical link of the samples of said signals representative of said motion, wherein the second swimming pool length is in a reverse direction of the first swimming pool length;

the processing circuitry further configured to generate a count of a number of detected at least one transient phases, wherein the generated count indicates a number of swimming pool lengths; and the processing circuitry further configured to cause the generated count to be sent in an output signal.

16. The device as claimed in claim 15, wherein the processing circuitry is further configured to:

detect a first transient phase in steady activity when the resultant signal along a single swimming pool length or a merged signal output becomes greater than a first threshold; and detect another transient phase in the steady activity when the resultant signal along the swimming pool length or the merged signal output, since a prior detection of a transient phase, has been lower than a second threshold and then is higher than said first threshold, wherein said second threshold being lower than said first threshold.

17. The device as claimed in claim 16, wherein the processing circuitry is further configured to establish a difference between two instants of said signals representative of the motion, and configured to determine a maximum energy component of differentiated signals, wherein the processing circuitry is further configured to detect another transient phase in the steady activity when a sign of said maximum component, when the merged signal is above said first threshold, is opposite to a sign of said maximum component in a preceding detection.

* * * * *